(12) United States Patent
Saaski et al.

(10) Patent No.: US 11,543,405 B2
(45) Date of Patent: Jan. 3, 2023

(54) ENVIRONMENTAL SAMPLING AND ASSAY DEVICE

(71) Applicant: CBRN INTERNATIONAL, LTD., Dubai (AE)

(72) Inventors: Elric Saaski, Monroe, WA (US); Robert Fay Livingston, St. George, UT (US); Duane M. Fox, Snohomish, WA (US)

(73) Assignee: CBRN INTERNATIONAL, LTD., Dubai (AE)

( * ) Notice: Subject to any disclaimer, the term of this patent is extended or adjusted under 35 U.S.C. 154(b) by 394 days.

(21) Appl. No.: 16/889,684

(22) Filed: Jun. 1, 2020

(65) Prior Publication Data
US 2020/0292533 A1  Sep. 17, 2020

Related U.S. Application Data

(63) Continuation of application No. 16/211,744, filed on Dec. 6, 2018, now Pat. No. 10,690,660, which is a
(Continued)

(51) Int. Cl.
*G01N 1/00* (2006.01)
*G01N 33/53* (2006.01)
(Continued)

(52) U.S. Cl.
CPC .............. *G01N 33/53* (2013.01); *C12M 1/34* (2013.01); *C12Q 1/04* (2013.01); *C12Q 1/70* (2013.01);
(Continued)

(58) Field of Classification Search
None
See application file for complete search history.

(56) References Cited

U.S. PATENT DOCUMENTS 4,979,821 A    12/1990  Schutt et al.
5,209,903 A *   5/1993  Kanamori ........ G01N 35/00029
                                                422/65
(Continued)

OTHER PUBLICATIONS

Genprime D-Cipher-151229, http://www.genprime.com/doa-test-reader.
(Continued)

*Primary Examiner* — Jyoti Nagpaul
(74) *Attorney, Agent, or Firm* — Timothy E. Siegel Patent Law, PLLC; Timothy E. Siegel

(57) ABSTRACT

An environmental sampling and assay system, having a coupon storage assembly, storing coupons; an environment sampling assembly, the sampling assembly mixing an environmental sample with a liquid to create a sample-liquid, bearing the environmental sample; a coupon moving assembly; a coupon wetting assembly for automatically wetting a coupon with the sample-liquid; a coupon perceiving device; a data input, adapted to receive a signal; and a data processing and control assembly, controlling the environmental sampling system, the coupon moving assembly, the wetting assembly and the coupon perceiving device. Further, the coupon moving assembly can retrieve a coupon from the coupon storage assembly and move it in a linear manner to the coupon wetting assembly.

17 Claims, 8 Drawing Sheets

Related U.S. Application Data continuation of application No. 15/708,073, filed on Sep. 18, 2017, now Pat. No. 10,197,558.

(60) Provisional application No. 62/395,596, filed on Sep. 16, 2016.

(51) Int. Cl.

| | | |
|---|---|---|
| *G01N 1/22* | (2006.01) | |
| *C12M 1/34* | (2006.01) | |
| *C12Q 1/04* | (2006.01) | |
| *C12Q 1/70* | (2006.01) | |
| *G01N 35/00* | (2006.01) | |
| *G01N 1/38* | (2006.01) | |
| *G01N 1/26* | (2006.01) | |
| *G01N 1/02* | (2006.01) | |

(52) U.S. Cl.
CPC .............. *G01N 1/2273* (2013.01); *G01N 1/38* (2013.01); *G01N 35/00029* (2013.01); *G01N 1/26* (2013.01); *G01N 2001/022* (2013.01); *G01N 2035/00089* (2013.01); *G01N 2035/00148* (2013.01); *G01N 2035/00891* (2013.01)

(56) References Cited

U.S. PATENT DOCUMENTS

| | | |
|---|---|---|
| 5,538,691 A | 7/1996 | Tosa et al. |
| 6,136,611 A | 10/2000 | Saaski |
| 6,615,763 B2 | 9/2003 | Edwards |
| 6,639,663 B1 | 10/2003 | Markle et al. |
| 6,910,445 B1 | 6/2005 | Manthei |
| 7,651,869 B2 | 1/2010 | Saaski |
| 7,678,338 B2 | 3/2010 | Sleeper |
| 8,131,477 B2 | 3/2012 | Li et al. |
| 8,411,916 B2 | 4/2013 | Hsieh et al. |
| 8,583,379 B2 | 11/2013 | Li et al. |
| 8,698,881 B2 | 4/2014 | Fleming et al. |
| 8,824,800 B2 | 9/2014 | Bremnes et al. |
| 8,865,089 B2 | 10/2014 | Blatt et al. |
| 8,889,424 B2 | 11/2014 | Ehrenkranz et al. |
| 8,916,390 B2 | 12/2014 | Ozcan et al. |
| 9,241,663 B2 | 1/2016 | Jena et al. |
| 9,386,221 B2 | 7/2016 | Kauniskangas et al. |
| 9,390,237 B2 | 7/2016 | Myers et al. |
| 9,600,878 B2 | 3/2017 | Tsai et al. |
| 10,197,558 B1 | 2/2019 | Saaski |
| 10,690,660 B2 | 6/2020 | Saaski |
| 2008/0304723 A1 | 12/2008 | Hsieh et al. |
| 2010/0304658 A1 | 12/2010 | Greevie |
| 2013/0280698 A1 | 10/2013 | Propper et al. |
| 2014/0065647 A1 | 3/2014 | Mamenta |
| 2015/0056719 A1 | 2/2015 | Karlovac et al. |
| 2016/0080548 A1 | 3/2016 | Erickson et al. |
| 2016/0131592 A1 | 5/2016 | Cooper |
| 2017/0300779 A1 | 10/2017 | Saaski |

OTHER PUBLICATIONS

Guardian Reader Manual, Alexeter Technologies, LLC, Wheeling, IL.

NIDS® Stand-Alone Reader III User Manual, Smiths Detection, Inc., Danbury, CT.

Tetracore Biothreat Alert Reader; http://www.tetracore.com/biowarfare/index.html.

Chemring, Joint Biological Point Detection Systems Overview, Apr. 9, 2003, http://www.chemringds.com/products/biological-detection/jbpds.aspx.

\* cited by examiner

ENVIRONMENTAL SAMPLING AND ASSAY DEVICE

RELATED APPLICATIONS

This application is a continuation of application U.S. Ser. No. 16/211,744 filed Dec. 6, 2018, which itself is a continuation of application U.S. Ser. No. 15/708,073 filed on Sep. 18, 2017, now U.S. Pat. No. 10,197,558 B1, issued Feb. 5, 2019, and claims benefit of provisional application U.S. Ser. No. 62/395,596 filed on Sep. 16, 2016, all of which are incorporated by reference as is fully set forth herein.

BACKGROUND

There is an ongoing concern about the possibility of biological or chemical substances being released into the air with the intent to harm people in the release area. Rapid detection of harmful substances is very helpful in meeting this threat, by speeding evacuation, inoculation, or the administration of an antidote. To meet this threat, with respect to biological substances, the Joint Biological Point Detections System (JBPDS) has been developed. This system includes an initial sensor that constantly monitors the air, and which triggers an assay test for biological substances, when some warning condition is encountered. Unfortunately, the JBPDS is bulky, and requires cooling and heating, making the entire system even bulkier. Because of these factors, it has not been packaged in a form that protects users from contamination. Moreover, only one size and shape of assay coupon or strip can be accepted into the JBPDS, blocking the use of many commercially available assay strips. Further, the assay reader does not check to determine that the assay strip has been properly wetted before the time period for an assay-read has elapsed, so that the full assay time period must elapse before a botched test can be detected. As noted, the JBPDS is configured to only detect biological, as opposed to chemical threats. Accordingly, the use of the JBPDS is hampered by a rigid requirement for assay coupons that fit a predetermined geometry and that must be read in a predetermined manner. Personnel using the JBPDS are exposed to the biological substances, for which the JBPDS is testing.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In a first separate aspect, the present invention may take the form of an environmental sampling and assay system, having a coupon storage assembly, storing coupons; an environment sampling assembly, the sampling assembly mixing an environmental sample with a liquid to create a sample-liquid, bearing the environmental sample; a coupon moving assembly; a coupon wetting assembly for automatically wetting a coupon with the sample-liquid; a coupon perceiving device; a data input, adapted to receive a signal; and a data processing and control assembly, controlling the environmental sampling system, the coupon moving assembly, the wetting assembly and the coupon perceiving device. Further, the coupon moving assembly can retrieve a coupon from the coupon storage assembly and move it in a linear manner to the coupon wetting assembly.

In a second separate aspect, the present invention may take the form of a system for evaluating wetted coupons, having a camera for taking images of the coupon and a logic system for evaluating the images. Further, the logic system evaluates the images to determine if the coupon has been properly wetted.

In a third separate aspect, the present invention may take the form of a coupon wetting system, having a sample cup having a top opening, and holding sample liquid; a pipetting system, including a pipette and reservoir, above the top opening; a coupon storage and movement assembly; and a control system, controlling the pipetting system, and the coupon storage and movement assembly. Further, wherein the control system controls the pipetting assembly to draw sample liquid through the pipette into the reservoir, and controls the coupon storage and movement assembly to move a coupon to a position directly under the pipette; and controls the pipetting system to wet the coupon with the sample fluid.

In addition to the exemplary aspects and embodiments described above, further aspects and embodiments will become apparent by reference to the drawings and by study of the following detailed descriptions.

BRIEF DESCRIPTION OF THE DRAWINGS

FIG. 2a is a multichannel biological assay coupon showing the strong presence of one targeted pathogen.

FIG. 2b is a multichannel biological assay coupon showing the weak presence of the aforementioned targeted pathogen, or an early indication of the targeted pathogen.

DETAILED DESCRIPTION OF THE PREFERRED EMBODIMENTS

Figure 1A:
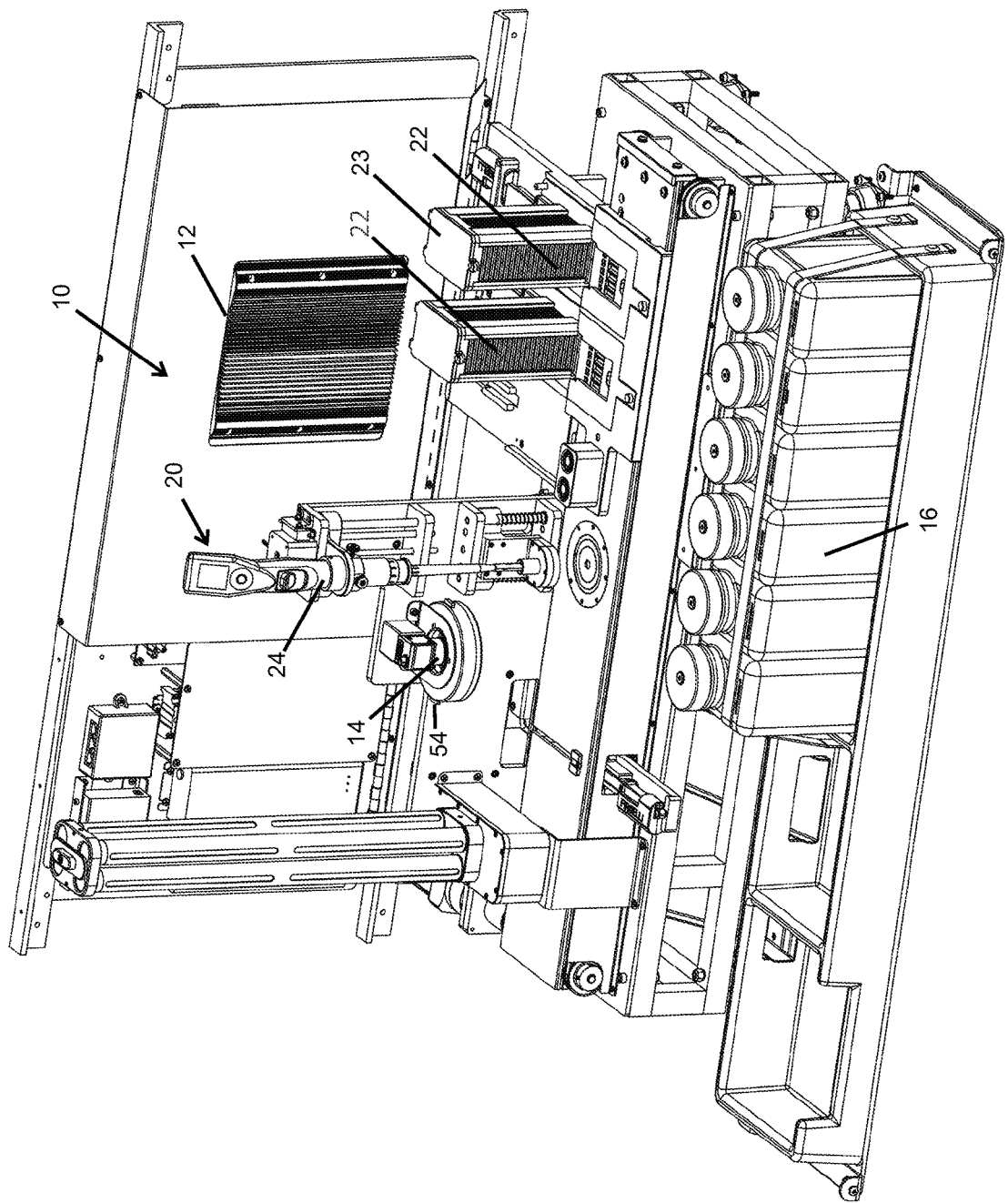
FIG. 1a is a front isometric view of an environmental sampling and assay device, according to the present invention.

Definition: In this application the word, "substance" may refer to an organism, such as a microbe.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 1B:
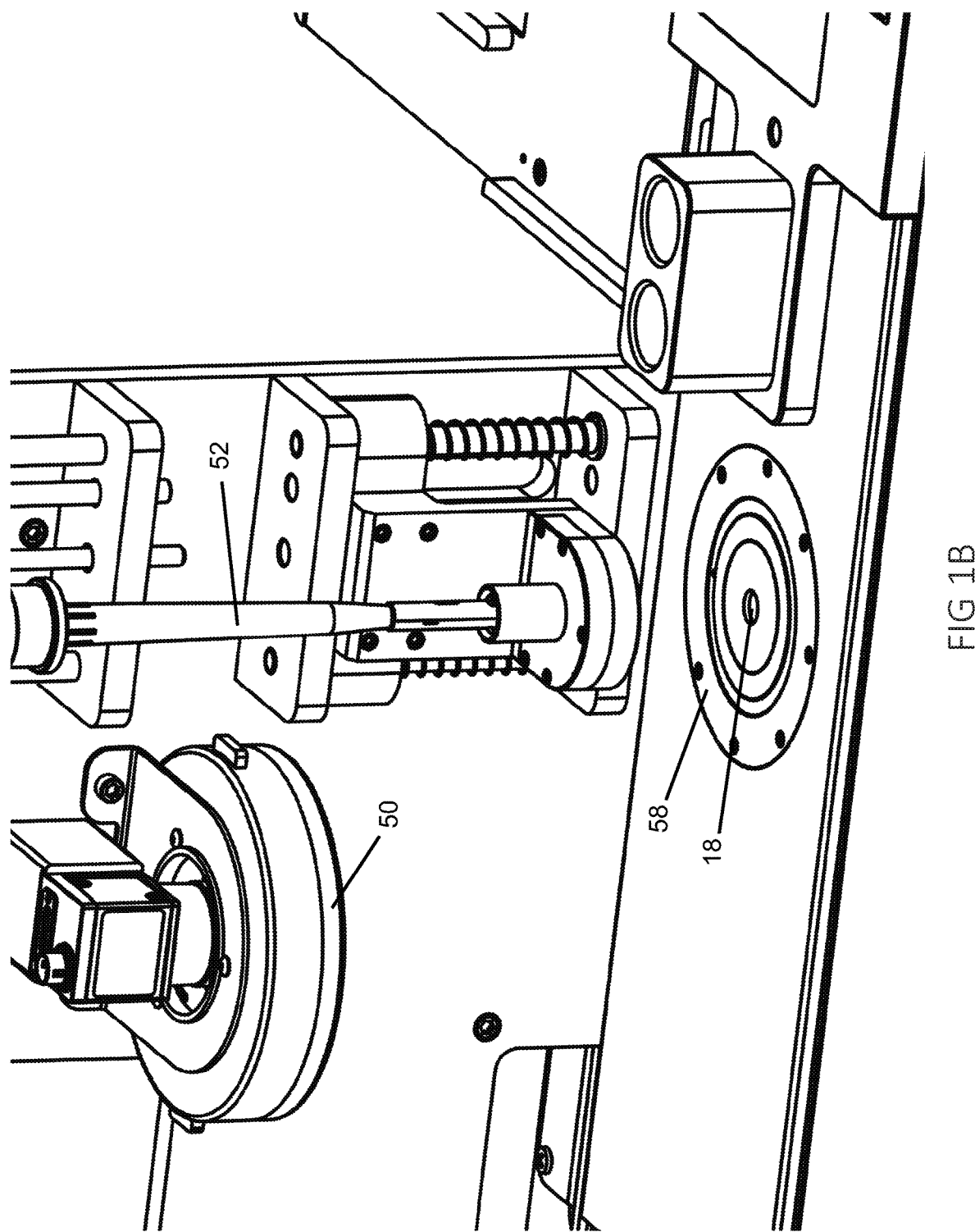
FIG. 1b is a detail view of FIG. 1, from the same perspective, showing the wetting assembly.
Figure 3:
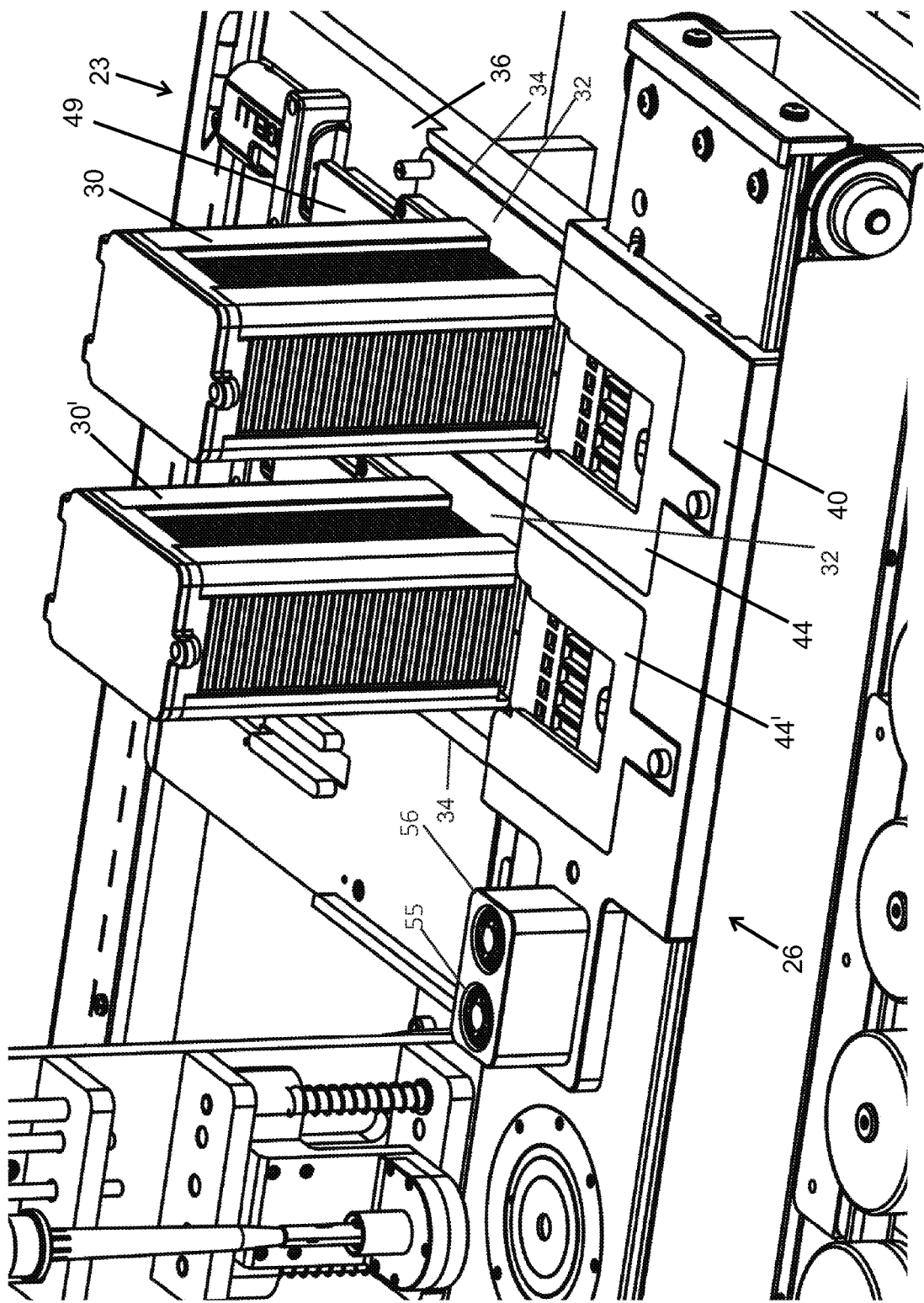
FIG. 3 is a detail view of FIG. 1, from the same perspective, showing the coupon storage assembly and coupon moving assembly.
Figure 4:
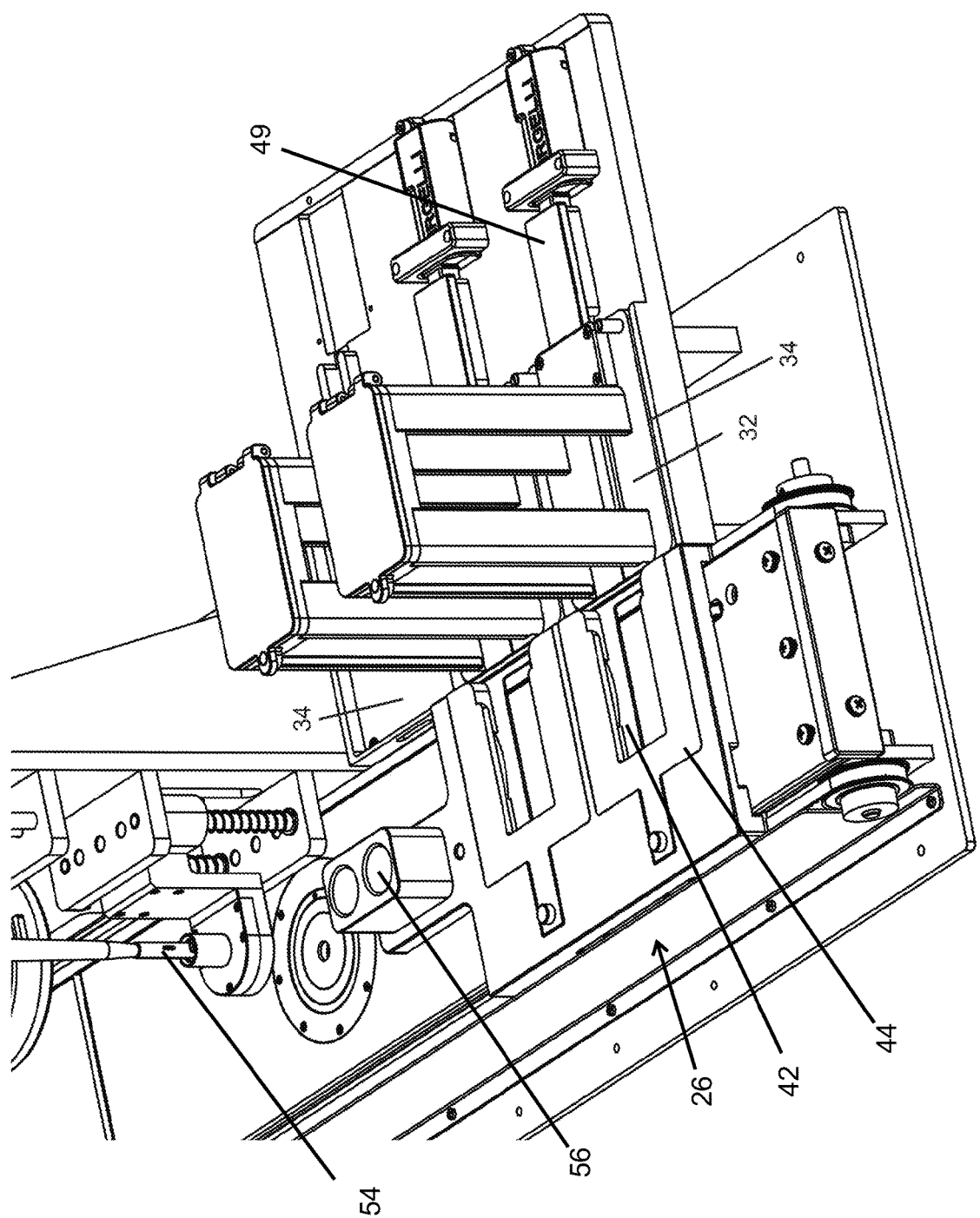
FIG. 4 is a detail view of the device of FIG. 1, from a rotated perspective, showing further features of the coupon storage assembly.
Figure 5:
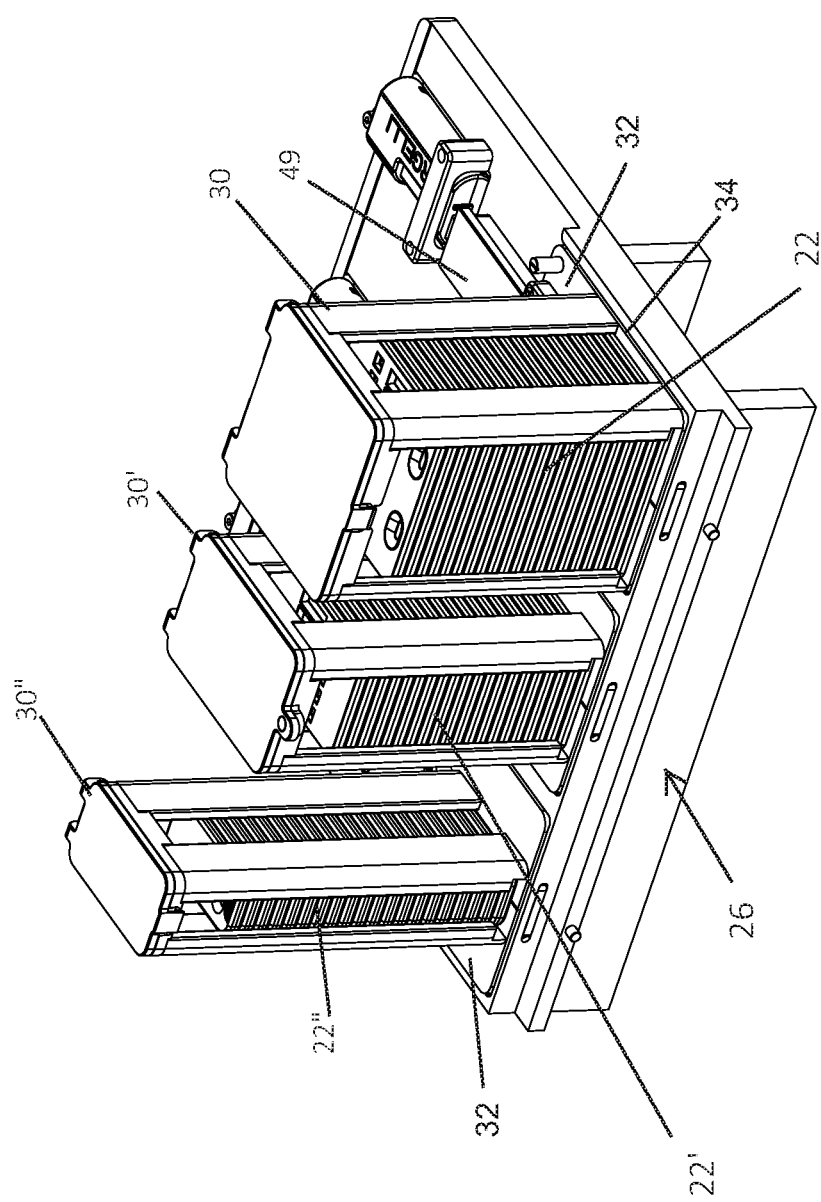
FIG. 5 is a partial view of the device of FIG. 1 placed into a different configuration in which coupon magazines having differing dimensions hold coupons having differing dimensions.

In broad overview, referring to FIGS. 1a, 1b, 3 and 6 in a preferred embodiment of an environmental sampling and assay formation system 10, a data processing and control assembly 12, controls the various elements of the system 10, to be detailed below, and processes imagery formed by a coupon perceiving device, such as a digital camera 14, to determine possible presence of biological or chemical contaminants, as will also be described further, below. After a detection cycle is triggered by input received over a data input assembly 68, from a preliminary detection system 70 (FIG. 6), an environmental sample (air, water or solid) is mixed with buffer from bottles 16 to form a sample liquid bearing environmental substances held in a sample cup 18 (FIG. 1b). Bottles 16 also hold deionized water, bleach, and waste, which may also be mixed with a sample. A pipetting assembly 20 (which may also be referred to as a wetting assembly) withdraws sample liquid from the sample cup 18 and delivers sample liquid to coupons 22 (sometimes also referred to as "tickets" in the industry) that are brought from a storage assembly 23, to a wetting position directly below the pipette 24 by the coupon movement assembly 26 (FIGS. 3-5). Movement assembly 26 then moves the coupons 22 to a position under the camera 14, and coupon perceptions, such as digital images, are formed at least every minute, with assembly 12 analyzing these coupon perceptions to detect a coupon indication of the presence of a target substance. A human-perceptible advisory issuing device issues a signal at any point that such an indication is detected. The advisory may include a visual or auditory cue.

A number of manufacturers produce coupons having various shapes and sizes and are designed to detect various differing biological substances. Some coupons 22 include an array of detection areas, one for each of as many as 8 different pathogens, or more. Much of this technology is proprietary, so that for many biological substances of concern there is only one coupon size (and shape) available that can be used to test for the substance. Accordingly, there is no single coupon size that could be used to detect all biologic substances of concern. Consequently, in order to detect the broadest possible range of biological substances, different sized coupons must be accepted.

Figure 6:
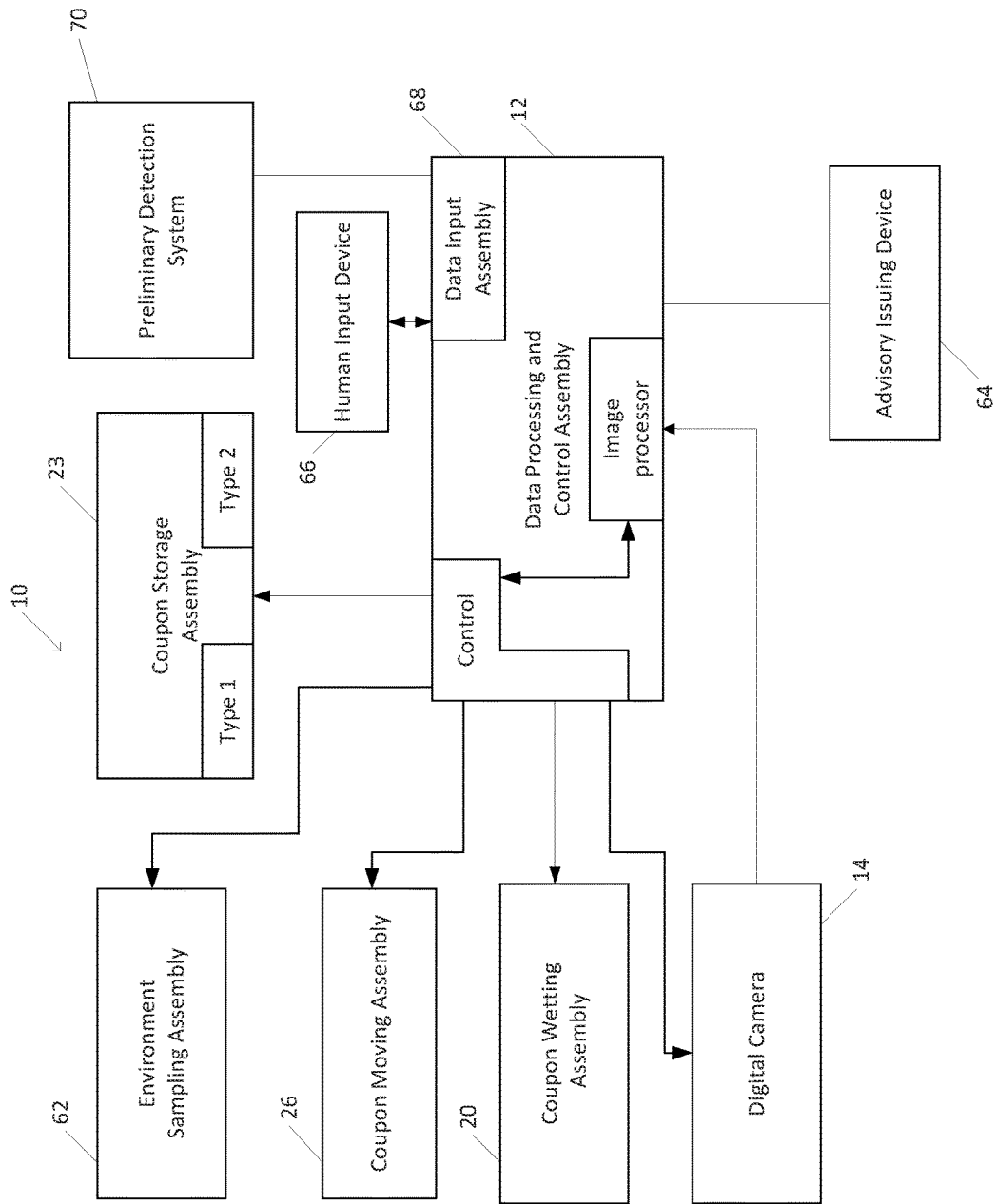
FIG. 6 is a block diagram, of the environmental sampling and assay device of FIG. 1, showing the communications connections between different parts of the device.

Referring to FIGS. 5 and 6, to meet this need, storage assembly 23 includes differently shaped coupon magazines 30 provided as part of system 10. Each of the magazines 30, however, has a standard shaped base 32 (FIG. 3), that is adapted to fit into a standard sized opening 34 (shown empty of magazine 30, in FIG. 3) in a support plate 36, thereby permitting a user to exchange first magazine 30, accommodating a stack of first sized coupons 22, for different magazines 30' and 30", that accommodate different sizes of coupon 22' and 22". Standard sized base 32 and standard sized opening 34 are mating features that permit any size magazine, having the standard sized base 32 to attach to storage assembly 23 at a standard sized opening 34 (also a mating feature). Other mating features that achieve the same purpose, for example matching posts and sockets, could serve the same function. Referring to FIG. 3, in like manner, a coupon carriage 40 has standard sized openings 42 (FIG. 4), in which can fit a first coupon carrier 44, holding first sized coupon 22, or a second coupon carrier 44' adapted to hold the second sized coupon 22', and third sized coupon 22" (FIG. 5). Although magazines 30 and 30' and carriers 44 and 44' appear to be the same in FIG. 3, they may in fact be different, to accommodate the different magazines 30, 30' and 30" and coupons 22, 22' and 22" shown in FIG. 5.

Coupons 22 are stacked along their dimension of least extent to permit the greatest number of coupons 22 to be stored in the magazines 30.

Once system 10 has been configured and is ready to operate, when an indication is received from the preliminary detection system 70, coupons 22 that are in a load position at the bottom of the magazine 30 are loaded by linear actuator mechanisms 49, (which are also a part of storage assembly 23) from magazines 30 into carriers 44. Gravity causes the next coupon 22 in each magazine 30 to descend into the load position from which it can be delivered to a carrier 44, next. Coupons 22 are then moved to a position beneath camera 14 to check for correct coupon loading. If this test is passed, pipette assembly 20, which includes an electronic pipette 24 (controlled by assembly 12), having a disposable reservoir 52 and needle (not shown), extending downwardly from the end of reservoir 52, takes up to 5 cc's of sample liquid from the sample cup 18, and uses this to fill the coupon reservoirs for coupons 22. After this filling, the coupons 22 are, for the first few minutes, checked by camera 14 every 30 seconds to verify proper wetting of the coupon 22, typically by checking to confirm that the control pattern is beginning to appear. If this is not achieved, the test may be aborted, and restarted, depending on which coupon 22 was not properly wetted and the logic programming of assembly 12. Alternatively, a human operator is informed and makes the decision to continue or restart. If the test continues (as it generally will) the coupons 22 are placed under camera 14 once every minute (illuminated by a light or flash ring 50), thereby providing enough slack time to fill two sample vials 55 held in carrier 56, with as skilled persons will readily recognize, liquid sample.

Many coupons 22 include a control pattern (typically a stripe) that develops when wetted, even in the absence of a target substance, for purposes of comparison. In a preferred embodiment, this pattern is read by digital camera 14 and used in comparison with the pattern that develops only in the presence of the target substance, in order to form a detection. It is, however, not entirely necessary to compare the test pattern with the control pattern, as in another preferred embodiment, a digitized target pattern (an image of a developed coupon) is introduced into the memory of assembly 12. This data entry may be performed by placing a developed coupon 22 or a control section into system 10 during system configuration and using a user interface (not shown) to command system 10 to use a digital camera 14 to take a digital photograph of the developed coupon 22 and store it in memory, properly labeled as a digitized image of a target pattern. In another preferred embodiment, system 10 is provided with digitized target images already stored. Otherwise digitized target images may be introduced into system 10 by way of the data input assembly 68.

Figure 2A:
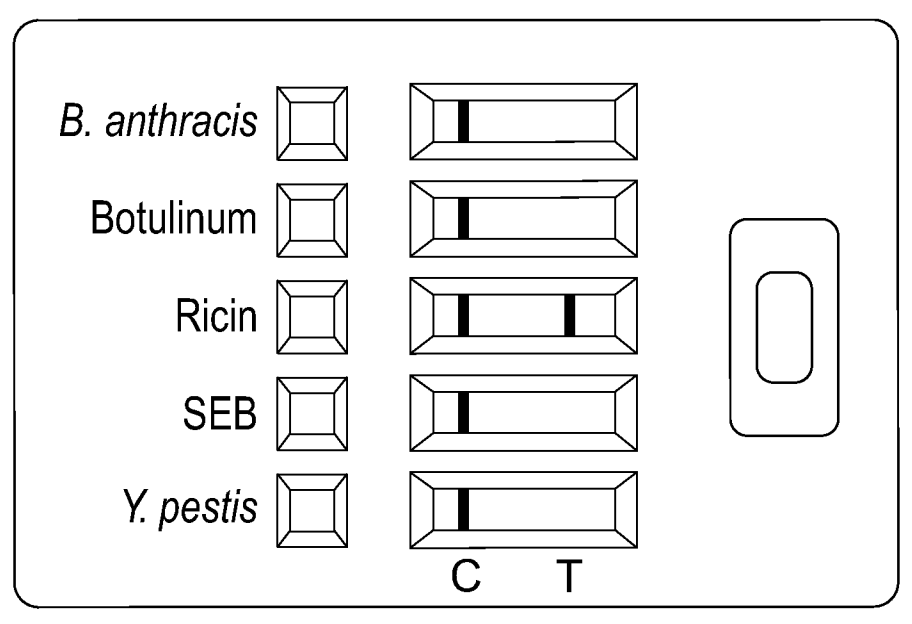
Figure 2B:
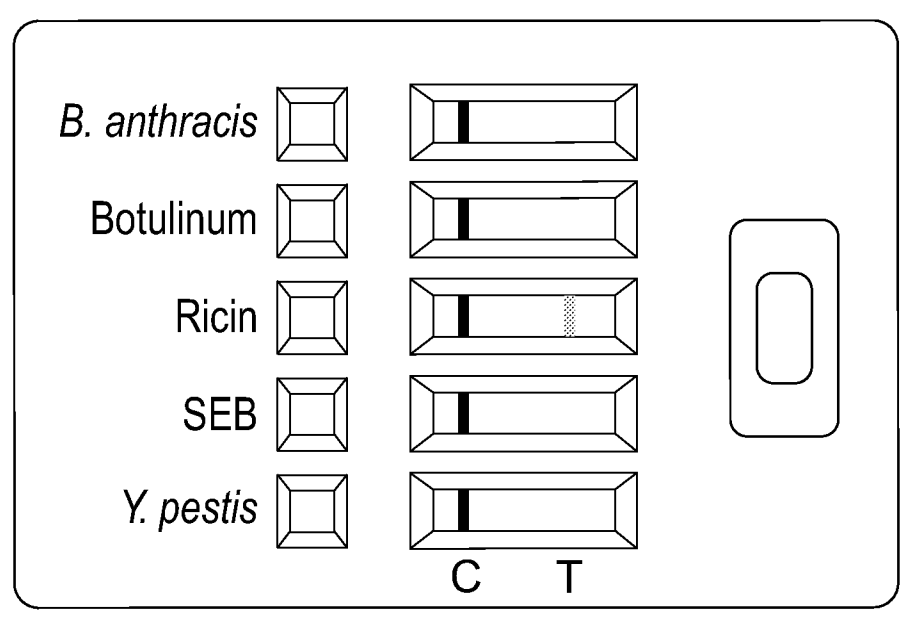

Assembly 12 compares each image with the digitized target image stored in its memory, or with the control pattern as perceived by the digital camera 14. Although coupon manufacturers specify a development time that is typically permitted to elapse before a human user reads the coupon, in a preferred embodiment, coupon examination by camera 14 and data processor 12 begins long before this time period has elapsed, with a target substance detection, also determined minutes before the development time has passed. In one embodiment, if the target substance is at a concentration that is at least 20% above the minimum level that can be detected by the coupon 22 after the full manufacturer's specified coupon development time has passed, the system provides an advisory signal prior to the passage of the full manufacturer's specified development time. This provides human operators with a quicker result that could in some circumstances be very important. In one embodiment, each pixel is compared with a threshold that is one-tenth of the intensity of the fully developed target pattern (dark if the developed target pattern is dark and light if the developed target pattern is light) if 95% of the pixels in the target pattern area pass this threshold and less than 5% of the pixels outside of the target area pass this threshold, then a detection is determined and a human perceptible indication, such as an auditory signal and/or visual signal is provided, to alert any nearby people that the target substance has been detected. Many other algorithms, including least squares detection and various linear algorithms are used in alternative embodiments. FIG. 2a is an illustration of a test pattern, and FIG. 2b is an illustration of a partially developed coupon 22, showing an indication of the test pattern of FIG. 2a. In one preferred embodiment, a coupon test pattern developed to the contrast level shown in FIG. 2b is sufficient to trigger an alarm.

The use of digital camera 14 provides a much greater flexibility of use, compared with some prior art systems in which a less robust reader has been used. In a preferred embodiment, assembly 12 is programmed to detect the change in hue that chemical detecting coupons present as an indication of the detection of a chemical substance. Also, carriers 44 are provided that can accept the size and shape of chemical coupons.

In one preferred embodiment, system 10 is housed in a vehicle interior that is essentially closed to the outside world and with positive air pressure (from air forced in from the outside and thoroughly filtered, on route) causing constant air flow from inside the vehicle interior to the outside through residual leaks, if any, thereby blocking airborne biological substances from entering the work area. System 10 is housed in a "glove-box," a largely transparent, air-tight box, having air-tight gloves sealed to apertures leading through the box walls. Ports lead from the glove box to the outside, to permit the gathering of air samples. Accordingly, a safe workspace is created for users of system 10.

The enclosure of the system 10 in an air-tight glove box is not limited to its use in a vehicle, but is used in many embodiments as it bears the advantage of protecting test personnel from potential hazards in the samples, a feature not usually provided in the prior art. One reason that prior art systems do not typically afford this level of protection to test personnel is that an air-tight enclosure may result in the buildup of water vapor in the glove box due to the handling of water borne samples. Such handling inevitably leads to evaporation of water into the closed glove box volume, creating a risk that water condensation onto optics or electronics may occur with deleterious effects on operation. In a preferred embodiment, the humidity is monitored by assembly 12 and a dehumidifier is turned on as needed to create an optimal or at least not dangerous, humidity level. Due to a desire to maximize operational time and minimize equipment failures, a solid-state dehumidifier using a thermoelectric module and free convection heat transfer is preferred, eliminating the need for a compressor or air moving fan. Dehumidifiers of this type are described at www.myivation.com and are available from Amazon.com under the Ivation trademark.

In another preferred embodiment, sample cup 18 is sterilized by exposure to ultraviolet light from four LEDs (not shown), which are part of UV-C sterilization system 58. The system 58 is positioned such that both the sample cup 18 and the tops of bottles 16 are sterilized using an intensity of about 96 mW/cm$^2$ at 280 nm for 5-20 seconds.

Referring, now, to FIG. 6, system 10 includes the previously noted data processing and control assembly 12, that controls the digital camera 14, the coupon wetting system 20, the coupon storage assembly 23 and the coupon moving assembly 26 to select a coupon 22, which is then wetted and moved to a position where the digital camera 14, in conjunction with data processing assembly 12, can monitor its development. Prior to these actions, however, an environment sampling system 62 must form a liquid sample from ambient air, or from a liquid that is accessible by system 10, or even from a solid sample, said liquid sample being then entered into a sample cup 18 from which the wetting assembly 20 draws liquid (using a pipette), and uses it to wet a coupon 22. If a target substance (or pathogen) is detected, then an advisory issuing device 64, which could be an auditory or visual announcement system, or both, is used to let an operator know that this has happened. A human input device 66 can be used by a human operator to command a particular test cycle. In one embodiment, device 66 is a laptop, tablet or other form of computer that connects with the rest of system 10 either through a USB port, ethernet port (which in a preferred embodiment is fiberoptic), or a wireless connection such as an RF connection, which may conform to either a Bluetooth or WIFI protocol. In another embodiment, device 66 is a custom-made input device, having a keypad and display. In some embodiments, there is overlap between input device 66 and advisory issuing device 64, with the display screen of device 66 used for the issuance of advisories. In yet another embodiment, as noted above, the preliminary detection system 70, for example an aerosol particle and bioluminescence detector such as the TacBio trigger developed by the US Army, is connected to the data input assembly 68 of system 10 and is able to command system 10 to begin a test of a particular type when an aerosol quality is found that meets a set of criteria. For example, when a biological particle count above a specified level is found, or if the particles have luminescent properties that fit in a prespecified range. The preliminary detection system 70 is fed by an aerosol sampler or aerosol concentrator. In one embodiment, the aerosol concentrator has an air throughput of 4,000 liters per minute and extracts aerosol particles from sampled air and injects them into a secondary circuit flowing at a much slower rate that is compatible with devices used for creating liquid samples. Environment sampling system 62 taps into this flowing aerosol concentrate with a 300 liter per minute cyclone wet sampler, to prepare a liquid sample for coupon wetting.

All of the assemblies noted in the discussion above have varying embodiments not specifically mentioned. In an alternative embodiment, the coupon wetting assembly 20 wets the coupons 22 by way of small disposable sponges. The coupon moving assembly 26 makes use of small electric vehicles that are optically guided. The coupon storing assembly 23 stores coupons 22 on turntables. Moreover, it should be noted that there are many forms of digital cameras, including linear cameras that simply scan back and forth with one line of pixels, two dimensional digital cameras and video cameras, all of which are perceiving devices. In a preferred embodiment, the perceiving device is a fiber optic cable, that is connected to a charge coupled device at the processing and control assembly 12. In a preferred embodiment, processing and control assembly 12 includes one or more digital computers, which may be in the form of a microcontroller and/or microprocessor, of digital signal processing chip or chips. In a preferred embodiment, processing and control assembly 12 includes non-transitory computer readable memory that has a program that controls the remainder of system 10 to perform the tasks disclosed and claimed herein. Assembly 12, in embodiments, also includes analog-to-digital convertors and digital-to-analog convertors and amplifiers, sufficient to produce control signals for controlling the various systems described.

While a number of exemplary aspects and embodiments have been discussed above, those possessed of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. An environmental sampling and assay system, comprising;
   (a) a coupon storage assembly, storing coupons;
   (b) an environment sampling assembly, said sampling assembly mixing an environmental sample with a liquid to create a sample-liquid, bearing said environmental sample;
   (c) a coupon moving assembly;
   (d) a coupon wetting assembly for automatically wetting a coupon with said sample-liquid;
   (e) a coupon perceiving device;
   (f) a data input, adapted to receive a signal;
   (g) a data processing and control assembly, controlling said environmental sampling system, said coupon moving assembly, said wetting assembly and said coupon perceiving device; and
   (h) wherein said coupon moving assembly can retrieve a coupon from said coupon storage assembly and move it in a linear manner to said coupon wetting assembly.

2. The system of claim 1, wherein said coupon storage device stores a first coupon type and a second coupon type, and wherein said first coupon type permits the detection of a specific pathogen and said second coupon type permits the detection of a chemical.

3. The system of claim 1, wherein control system responds to a said signal by commanding said coupon storage and movement assembly move a coupon to a location where it can wetted by said wetting system.

4. The system of claim 3, wherein said coupon storage and movement assembly moves said coupon in a linear manner.

5. The system of claim 3, wherein said coupon storage and movement assembly, includes a coupon storage assembly, and a coupon moving assembly which removes a coupon from said coupon storage assembly and moves said coupon to said wetting assembly, when said control system commands said wetting system to wet a coupon.

6. The system of claim 1, wherein said coupon storage device stores a first coupon type and a second coupon type, and wherein said first type of coupon has a first shape and said second type of coupon has a second shape.

7. The system of claim 6, wherein said coupon movement assembly pushes said coupon onto a coupon carriage.

8. The system of claim 1, wherein said coupon storage assembly stores said coupon in a vertical magazine, and wherein said coupon moving assembly retrieves a coupon by pushing a bottom most coupon out of said magazine, permitting coupons above it to move down by force of gravity.

9. The system of claim 8, wherein said coupon carriage also includes a holder for at least one vial.

10. The system of claim 8, wherein after said coupon movement assembly pushes said coupon onto said coupon carriage said movement assembly moves said coupon to said coupon wetting assembly.

11. The system of claim 1, wherein said environment sampling system includes a plurality of bottles holding different liquids for mixing with said environmental sample.

12. The system of claim 11, further wherein if there is no determination that the coupon has not been properly wetted, said coupon is further tested to determine the presence of a substance, but if improper wetting is detected said coupon further testing is discontinued.

13. The system of claim 12, further wherein after said coupon is wetted said coupon storage and movement assembly moves said coupon away from said pipetting system.

14. The system of claim 13, further wherein after said coupon is moved away from said pipetting system, said pipetting system fills a sample vial with said liquid sample.

15. The system of claim 13, wherein after said coupon is moved away from said pipetting system, said pipetting system fills two sample vials with said liquid sample.

16. A system for evaluating wetted coupons, comprising:
   (a) a camera for taking images of said coupon;
   (b) a logic system for evaluating said images; and
   (c) wherein said logic system evaluates said images to determine if said coupon has been properly wetted.

17. A coupon wetting system, comprising:
   (a) a sample cup having a top opening, and holding sample liquid;
   (b) a pipetting system, including a pipette and reservoir, above said top opening;
   (c) a coupon storage and movement assembly;
   (d) a control system, controlling said pipetting system, and said coupon storage and movement assembly; and
   (e) wherein said control system controls said pipetting assembly to draw sample liquid through said pipette into said reservoir, and controls the coupon storage and movement assembly to move a coupon to a position directly under said pipette; and controls said pipetting system to wet said coupon with said sample fluid.

* * * * *